United States Patent [19]
Uchiyama et al.

[11] Patent Number: 5,843,658
[45] Date of Patent: Dec. 1, 1998

[54] METHOD OF MEASURING OLIGONUCLEOTIDE DECOMPOSING ACTIVITY

[75] Inventors: Hisatoshi Uchiyama; Masaki Jibu; Kenichi Hirano, all of Hamamatsu; Kazunari Taira, Tsukuba, all of Japan

[73] Assignee: Hamamatsu Photonics K.K., Shizuoka-ken, Japan

[21] Appl. No.: 612,069

[22] Filed: Mar. 7, 1996

[30] Foreign Application Priority Data

Mar. 10, 1995 [JP] Japan .................................. 7-050926

[51] Int. Cl.$^6$ ............................... C12Q 1/68; C12P 19/34

[52] U.S. Cl. ............................................. 435/6; 435/91.2

[58] Field of Search .................. 435/6, 91.2; 935/77, 935/78

[56] References Cited

U.S. PATENT DOCUMENTS 5,037,615  8/1991  Kane ..................................... 422/82.08
5,607,834  3/1997  Bagwell ..................................... 435/6

FOREIGN PATENT DOCUMENTS

0428000A1  5/1991  European Pat. Off. .
2278356   11/1994  United Kingdom .

OTHER PUBLICATIONS

Ghosh et al, Nucleic Acid Res. 22(15):3155–3159, 1994.
Leonetti et al, PNAS 88:2702–2706 (Apr. 1991).
R. A. Cardullo, et al., "Detection of Nucleic Acid Hybridization by Nonradiative Fluorescence Resonance Energy Transfer", Proceedings of the National Academy of Sciences of the USA, Dec. 1, 1988, vol. 85, No. 23, pp. 8790–8794, XP000453537.
Uchiyama, et al., "Detection of Undergraded Oligonucleotides in Vivo by Fluorescence Resonance Energy Transfer", The Journal Of Biological Chemistry, vol. 27, No. 1, Issue of Jan. 5, pp. 380–384, 1996.
Ju et al, "Fluorescence Energy Transfer Dye–Labeled Primers for DNA Sequencing and Analysis", Pro. Natl Acad. Sci. USA, vol. 92, pp. 4347–4351, May 1995 Biophysics.

*Primary Examiner*—Eggerton A. Campbell
*Attorney, Agent, or Firm*—Pillsbury, Madison & Sutro, IP Group of Cushman, Darby & Cushman

[57] ABSTRACT

The present invention provides an in situ monitoring of the decomposing activity against oligonucleotides target in a biological tissue. A single-chain oligonucleotide target comprises an appropriate number of nucleic acid bases to be examined with an energy donor and an energy acceptor respectively at its 5'- and 3'-terminals. Monitoring of the fluorescence changes of the target after injection into a biological tissue, particularly the fluorescent resonance energy transfer(FRET) phenomena between the energy donor and acceptor, indicates whether the oligonucleotide is not decomposed yet.

10 Claims, 8 Drawing Sheets

EMISSION WAVELENGTH (nm)

Fig. 5

EXCITATION WAVELENGTH (nm)

METHOD OF MEASURING OLIGONUCLEOTIDE DECOMPOSING ACTIVITY

BACKGROUND OF THE INVENTION

1. Field of the Invention

The present invention relates to a method of measuring the decomposing activity of oligonucleotides.

2. Related Background Art

As an effective means for studying how to control the expression of a target gene, for example, it has been known to inject a functional oligonucleotide into a cell of an organism to see how this oligonucleotide behaves within the cell (Erickson, R. P., and Izant, J. G. ed., 1992, Gene Regulation: Biology of Antisense RNA and DNA, Raven Press, New York; Murray, J. A. H. ed., 1992, Antisense RNA and DNA, Wiley-Liss, New York).

For example, it has been known that, when injected into a cell, short DNA molecules combine with their corresponding mRNAs which include complementary base sequences, thereby inhibiting the synthesis of a particular protein (Wagner, R. W., 1994, Nature 372, 333–335). Also, in the therapeutic study of AIDS, a specifically designed ribozyme has been known to cut the mRNA of AIDS virus (Sarver, N., et al., Science 247, 1222–1225, 1990), thereby suggesting that ribozymes and their synthetically modified analogues are candidates for useful drugs in the future.

SUMMARY OF THE INVENTION

However, the stability or reliability of these predetermined functional oligonucleotides within an organism largely depends on their sequence or number of bases as well as various biological materials such as nucleases existing therein.

Accordingly, there is a strong possibility that a functional oligonucleotide injected into an organism will be cut (or decomposed), for example, by a nuclease or the like within a cell. In this case, according to conventional techniques, it has been very difficult to detect whether the target oligonucleotide is decomposed or not.

Conventionally, in order to monitor an oligonucleotide within an organism, investigators have been used a probe made of an oligonucleotide whose one end is labeled with a fluorescence dye.

However, in such a technique, there is a possibility that, even when the probe does not have its aimed function as oligonucleotide any more after being decomposed by a decomposition reaction such as nucleolysis by a nuclease, the fluorescence of the dye in a decomposed fragment can still be detected.

Accordingly, the inventors have diligently conducted studies in order to overcome the foregoing problems and succeeded in developing a method by which changes in molecular structures of a subject oligonucleotide within a cell, such as its decomposition caused by a nuclease or the like, can be detected with high sensitivity. Then, based on this method, the inventors have succeeded in providing a method by which the stability or reliability of the subject oligonucleotide can be evaluated in vitro or in vivo.

Namely, the method of measuring the decomposing activity against a subject oligonucleotide in accordance with the present invention comprises the steps of labeling the oligonucleotide with two kinds of different fluorescenct dyes( or fluorochromes), and then inspecting a fluorescence characteristic based on an intramolecular fluorescence resonance energy transfer (FRET) [Stryer, L. (1978), Annu. Rev. Biochem., 47, 819–846.; Herman, B. (1989) In Taylor, D. L. and Wang, Y. (eds.), Fluorescence Microscopy of Living Cells in Culture-Part B. Academic Press, New York, pp. 220–245.] caused by these two kinds of fluorochromes.

More specifically, the present invention provides a method of measuring the decomposing activity against a single-stranded (or single chain) subject oligonucleotide in which the measurement is performed according to the detection of a fluorescence resonance energy transfer caused by a set of energy donor group and energy acceptor group combined with 5'- and 3'-terminals of the oligonucleotide.

Also, the present invention provides a measuring method in which the single-chain subject oligonucleotide comprises not less than 3 but not more than 20 nucleic acid bases. Further, the present invention provides a measuring method in which the single-chain subject oligonucleotide comprises 10 nucleic acid bases in particular.

Moreover, the present invention provides a method of measuring the decomposing activity against a single-stranded subject oligonucleotide based on the detection of a fluorescence resonance energy transfer caused by a set of energy donor group and energy acceptor group combined with 5'- and 3'-terminals of the oligonucleotide, while the energy donor group contains a fluorescein fluorochrome and the energy acceptor group contains at least a rhodamine fluorochrome.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS

In the following, the present invention will be explained further in detail.

(Decomposing Activity against Subject Single-Chain Oligonucleotide)

In the present invention, the decomposing activity against a subject single-chain oligonucleotide refers to the ability to decompose the subject sle-chain oligonucleotide by decomposition reaction under various conditions in vivo r in vitro, thereby exhibiting none of its original physiological action any more. For example, it refers to a case where the subject single-chain oligonucleotide is subjected to a single hydrolysis reaction so as to be divided into two. Regardless of whether or not the decomposing portion has been known beforehand, the subject single-chain oligonucleotide can be used in the present invention without any restriction. In cases where the decomposing portion has been known beforehand, it can be further confirmed whether or not such a portion has been subjected to such a reaction as cutting. In general, physiological activities observed in an oligonucleotide are lost or become very weak when at least a part of the oligonucleotide is lacking. Accordingly, it is important to know a change thereof and, in particular, to monitor it on real time.

(Fluorescence Resonance Energy Transfer, FRET)

The FRET in the present invention is a fluorescence phenomenon described in literatures (e.g., Stryer, L. Ann. Rev. Biochem., 47, 1978, 819–846; In Taylor, D. L. and Wang, Y. eds., Fluorescence Microscopy of Living Cells in Culture-Part B. Academic Press, New York, 220–245, 1989). In short, when (1) the fluorescence spectrum of one fluorogen (energy donor) overlaps with the excitation spectrum of the other fluorogen (energy acceptor) and (2) the donor and the acceptor are positioned close to each other, the excitation of the donor induces the fluorescence from the acceptor while reducing the fluorescence intensity resulting from the donor itself. The phenomenon is refered as FRET.

Also, the above-mentioned FRET is known to be quite sensitive to the distance between the donor and the acceptor and, in general, proportional to $10^{-6}$ of this distance.

Figure 1:
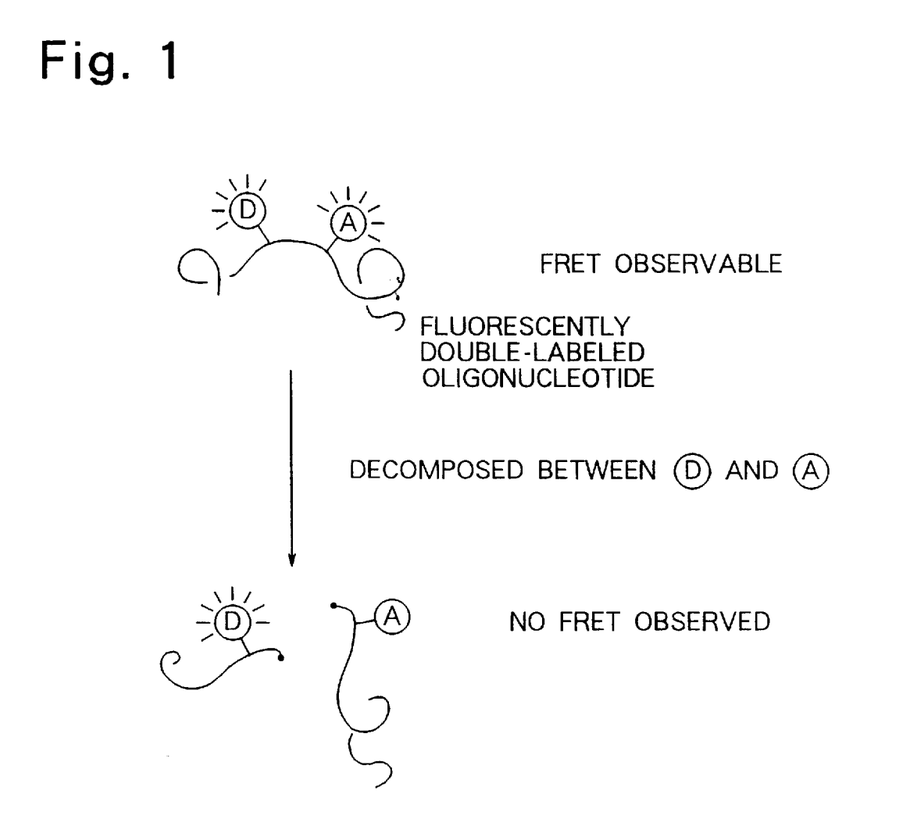
FIG. 1 is a schematic view explaining the principle of the present invention, in which the FRET observed on the basis of the relationship between the energy donor (D) and energy acceptor (A) combined with a subject oligonucleotide becomes unobservable due to a decomposition reaction.

Accordingly, when a set of donor and acceptor providing the FRET is disposed in a subject and the disappearance of the FRET occurring between the donor and the acceptor is monitored, it can be confirmed that the subject has suffered a great change in the distance between the donor and the acceptor, namely, a portion containing the donor group and acceptor group has been cut, for example, and is not in a single molecular any more (FIG. 1).

(Energy Donor and Energy Acceptor)

There is no particular restriction concerning the energy donor and energy acceptor which can be used in the present invention as long as they are in a combination which can utilize the above-mentioned FRET.

While dyes having various fluorochromes can be used, fluorescein and rhodamine dyes, for example, can be preferably used.

In particular, in the present invention, a dye having a fluorescein fluorogen and a dye having a rhodamine X fluorogen are preferably used as the donor and the acceptor, respectively. The absorption spectra of fluorescein and rhodamine X have absorption peaks at 497 nm and 586 nm, respectively. When excited at 494 nm, fluorescein exhibits a fluorescence peak at 523 nm. On the other hand, rhodamine X exhibits a fluorescence peak at 610 nm when excited at 585 nm.

In cases where there is an appropriate distance between these two kinds of fluorochromes for generating the FRET, as the fluorescence energy transfers from fluorescein which is the donor to rhodamine X which is the acceptor, the fluorescence intensity derived from fluorescein decreases while that derived from rhodamine X increases.

(Preparation of Subject Single-Chain Oligonucleotide)

In the present invention, the kind of base sequence in the single-chain oligonucleotide as the subject can be selected according to its purpose of use without being restricted in particular.

In order to utilize the FRET in the present invention, it is necessary for two kinds of fluorochromes to be disposed with a distance therebetween being within a certain preferable range. The number of base sequences in the oligonucleotide between these two kinds of fluorochromes is dependent on the selection of the fluorochromes which can utilize the FRET.

Accordingly, it is preferable to prepare a subject oligonucleotide such that above-mentioned two kinds of fluorochromes are cited at the appropriate portions thereof (holding therebetween a portion which will be cut upon a decomposition reaction). For example, when fluoescein and rhodamine X are used as the above-mentioned two kinds of fluorochromes respectively, the number of base sequences in the oligonucleotide therebetween is most preferably about 10. More generally, the oligonucleotide therebetween preferably comprises not less than 3 but not more than 20 nucleic acid bases. When it is too short, the position where the subject is decomposed may be quite limited; whereas, when it is too long, the FRET may not be observed sufficiently. Under these circumstances, its more preferable range comprises not less than 5 but not more than 18 (or, further preferably, not less than 8 but not more than 15) nucleic acid bases.

It is easy for one skilled in the art to synthesize an oligonucleotide having such a number of base sequences so as to include a position where a subject is decomposed, to select appropriate fluorochromes, and then to combine these fluorochromes with the oligonucleotide portion to prepare a subject oligonucleotide.

In the present invention, other than the oligonucleotide portion that is subjected to a decomposition reaction, there is no restriction about the molecular composition as long as this reaction is not influenced thereby.

Accordingly, groups such as those of an oligonucleotide or oligopeptide may be further combined with the 5'- or 3'-terminals of the subject oligonucleotide that is subjected to decomposition. Namely, as an embodiment of the present invention, the oligonucleotide of the above-mentioned predetermined number of base sequences including an estimated decomposing position of a single subject functional polynucleotide is selected and the above-mentioned fluorochromes by which the FRET can be utilized are combined with both ends thereof, thereby making it possible to trace a reaction in which such the position is decomposed. In this case, except for the above-mentioned polynucleotide portion, there is substantially no restriction.

Further, in the present invention, it is not always necessary for the subject to be a single chain at the time of being decomposed. It may complementarily form a double chain with other DNAs, for example, before being subjected to a decomposition reaction, whereby the above-mentioned change in FRET can be observed.

In the present invention, there is no particular restriction concerning the method by which the subject oligonucleotide is synthesized. Any known method for synthesizing nucleotides may be suitably used. For example, chemical synthesis methods or automatic synthesis methods may be used. Also, if necessary, synthesis methods using enzymes may be suitably used.

(Preparation of Subject Oligonucleotide Having Fluorochromes)

In the present invention, there is no particular restriction concerning the method of combining the energy donor group and the energy acceptor group with 5'- and 3'-terminals of the subject oligonucleotide portion. General organic synthesis methods or enzymatic reactions using appropriate derivatives may be used to prepare the subject oligonucleotide having fluorescence in various forms. Examples thereof will be explained in the following.

(1) In a method by which a desirable energy donor group and an energy acceptor group such as those described above are combined with a target oligonucleotide, the target oligonucleotide may be synthesized beforehand and then active groups at its 5'- and 3'-terminals (e.g., their OH or NH2 groups) may be combined with the energy donor groups and energy acceptor group by a known chemical reaction, thereby introducing these groups thereinto. A linker portion may be additionally inserted between the energy donor and receptor groups to be introduced and the terminal groups in order to attain an appropriate length.

(2) A double-labeled oligonucleotide is synthesized using two kinds of fluocently labeled mononucleotides as the substrates of the starting and ending reactions of the synthesis in order to incorporate florochromes at the both terminals of the subject oligonucleotide as the energy donor and acceptor.

In examples of the present invention, a fluorescein fluorochrome was combined with the 5'-terminal of oligonucleotide (10-mer) having a rhodamine X fluorochrome at its 3'-terminal by a chemical synthesis method.

Similarly, in the present invention, a mononucleotide having a fluorescein fluorochrome was combined with the 3'-terminal of oligonucleotide (9-mer) having a rhodamine X fluorogen at its 5'-terminal by an enzymatic chemical method.

(Measurement of Decomposing Activity by FRET Measurement)

In the present invention, there is no restriction concerning the method by which fluorescence spectra derived from two kinds of fluorochromes are measured and compared them with each other.

For example, FRET may be estimated by comparison between the ratio of the fluorescence intensity values derived from each of two fluorochromes under a condition in which the FRET is possible and the ratio of the fluorescence intensity values derived from each flurochromes under a condition in which the FRET does not occur.

In this case, in order to measure the FRET efficiency with higher sensitivity, selection of excitation wavelength, filters for selective measurement of fluorescence components, and means for simultaneously measuring two kinds of fluorescence components, for example, may be preferably used.

Also, when a phenomenon based on the FRET is influential to other phenomenons such as a change in the life-time of fluorescence, such a change in the life-time can be utilized in the measurement of decomposing activity in accordance with the present invention.

Further, in the present invention, any nucleolytic activity of enzymes can be estimated, regardless of whether it decomposes a single chain oligonucleotide or double chain oligonucleotide.

(Measurement of Decomposing Activity by FRET Measurement in Vivo)

In the method of measuring decomposing activity against an oligonucleotide in accordance with the present invention, there is no particular restriction concerning the measuring method in vivo.

Any means may be used as long as it can measure the fluorescence values derived from two kinds of fluorochromes. For example, while a sample is observed by visualization with a fluorescence microscope, two kinds of filters may be used to measure the fluorescence values derived from the two kinds of fluorochromes and monitor their temporal changes.

In the present invention, for example, an oligonucleotide (R-ODN-F) labeled with two kinds of fulorogens may be injected into a sea urchin egg such that its FRET can be observed in vivo.

As the FRET is observed, it can be confirmed in vivo that the oligonucleotide is not decomposed in a cell.

Also, when the FRET changes temporally time or according to other biochemical processings, the decomposing state of the oligonucleotide can be observed on real time.

The foregoing techniques provide means for measuring the decomposing activity of various kinds of nucleases against a subject oligonucleotide in vitro or in vivo.

Also, the stability and life-time of the subject oligonucleotide, for example, in a cell can be monitored on real time.

In the present invention prefered the FRET measurement systems under a microscope comprise a fluorescence microscope, the separation optics of fluorescence components, photo-detectors such as high sensitivity video cameras, and a computer for data analysis such as an image processor, where the fluorescence light from the microscope is separated into red and greencomponents through the separation optics filters(A) or through a dichroic mirror. In the present example of the invention described below, the red and green components of fluorescence from the same egg were separated through filters and accumulated with a high-sensitivityvideo camera. The fluorescence intensity was analyzed with a computer.

EXAMPLES

In the following, the present invention will be explained in detail with reference to its examples. Nevertheless, the present invention should not be restricted to these examples.

(Example 1)

Figure 7:
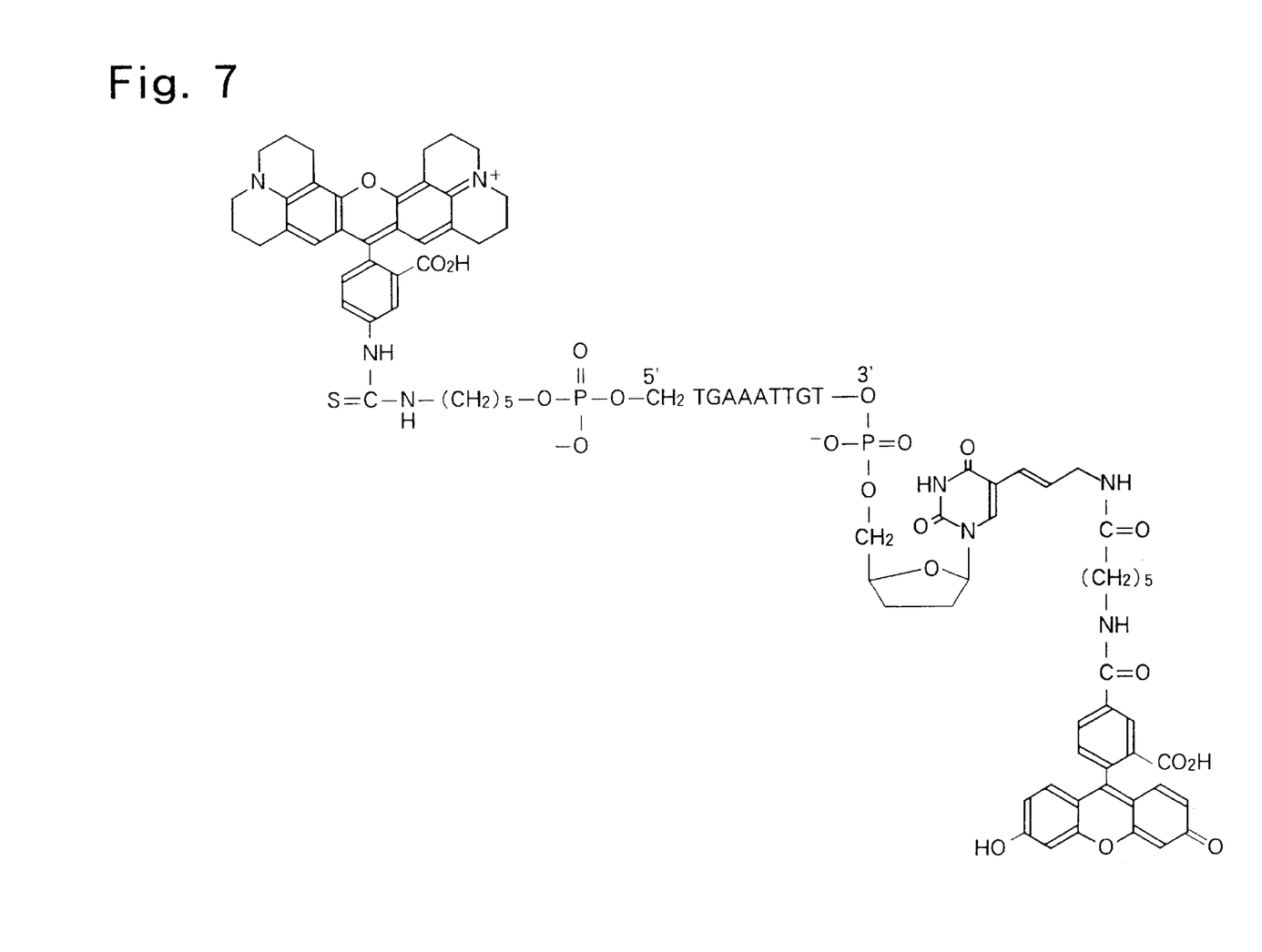
FIG. 7 is a chart showing the molecular structure of 5'-rhodamine-TGAAATTGTU-3'-fluorescein.

Synthesis of 5'-Rhodamine X-TGAAATTGTU-3'-Fluorescein (R-ODN-F) (FIG. 7)

R-ODN-F was synthesized from 3'-fluorescein-1, 2dideoxyuridine-5'-triphosphate (ddUTP-F) (manufactured by Boehringer Mannheim) and 5'-rhodamine X-TGAAATTGT-3'(R-ODN) (manufactured by Takara Shuzo) using the following enzymatic reaction.

Namely, 0.1 mM of ddUTP-F and 0.05 mM of R-ODN were incubated with 20 units of terminal deoxynucleotidyl transferase (manufactured by GIBCOBRL) in a mixture made of 100-mM cacodylic acid potassium buffer solution (pH 7.2), 2 mM of $CoCl_2$, and 1 mM of dithiothreitol (23) for 2 hours at 37° C.

The resulting R-ODN-F was purified and separated by a high-pressure liquid chromatography (HPLC, model 8100, manufactured by Tosoh) using an ion-exchange column (TSK gel DEAE-5PW, manufactured by Tosoh) under the following conditions:

Flow rate: 1.0 ml/min
Temperature: room temperature 25° C.
Solvent: linear concentration gradient using 0.1 M to 1 M of NaCl in 20-mM Tris-HCl buffer solution (pH 9.0)

Figure 8:
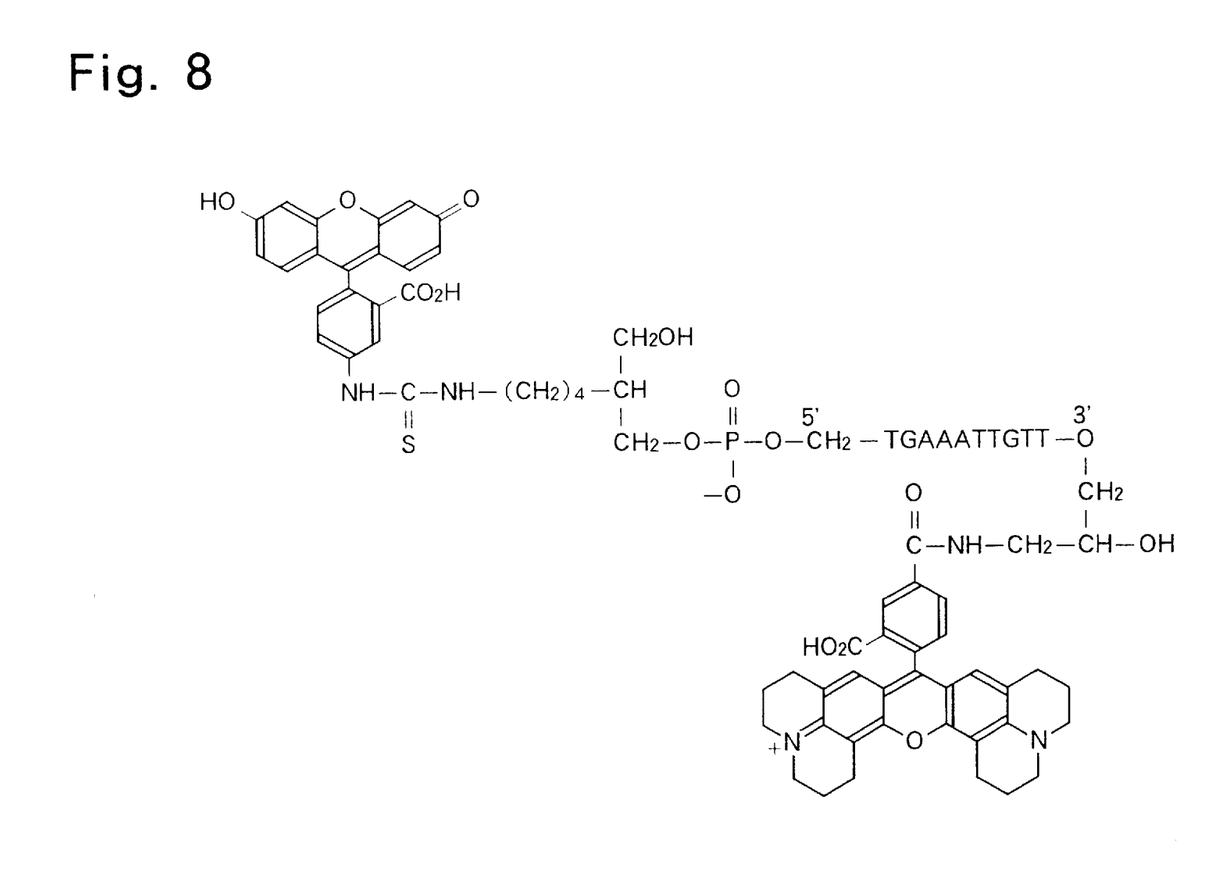
FIG. 8 is a chart showing the molecular structure of 5'-fluorescein-TGAAATTGTT-3'-rhodamine X.
Figure 9:
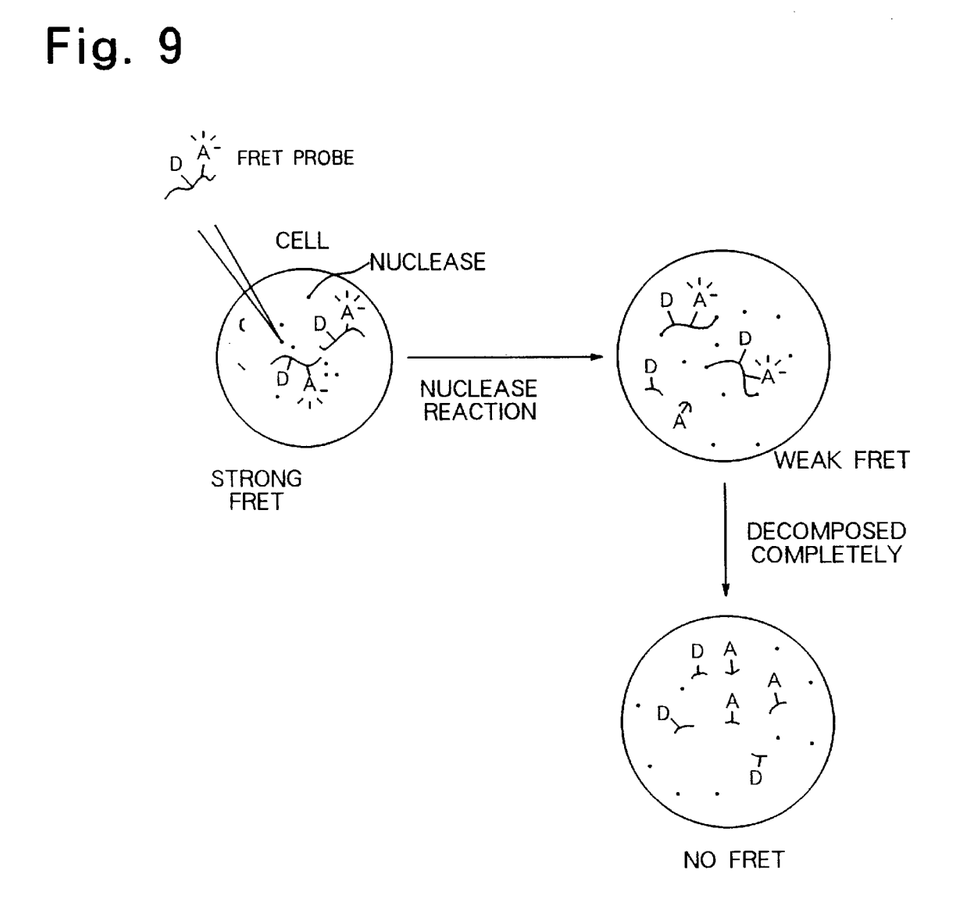
FIG. 9 is a schematic view explaining the operation of the present invention, in which a subject oligonucleotide by which the FRET becomes observable is injected into a cell and then the change in the FRET within the cell is monitored so as to trace the decomposition reaction caused by nucleases within the cell.
Figure 10A:
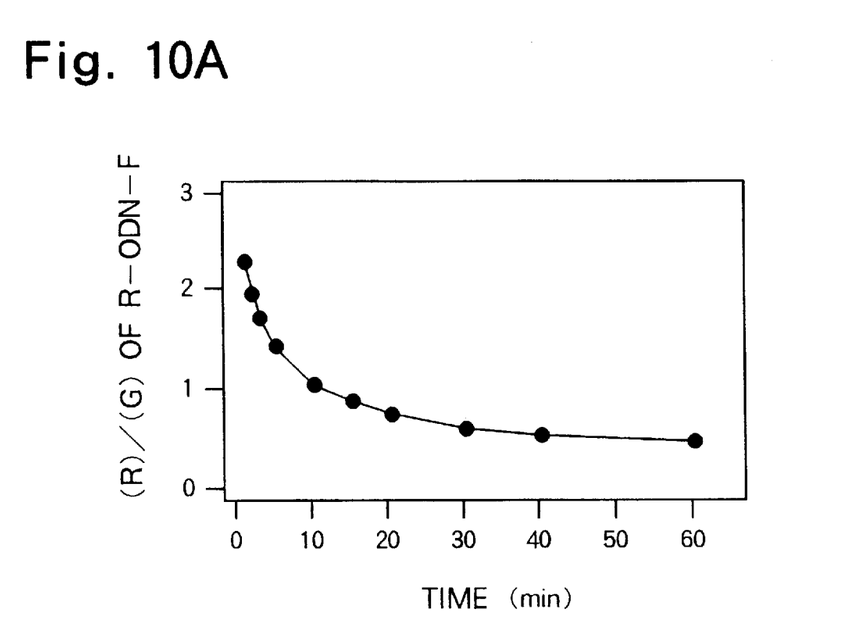
FIG. 10A is a chart showing changes in the ratio of two fluorescence components, i.e., red component/green component, from sea urchin eggs over time under a fluorescence microscope, in which A showing the change in the ratio in a sea urchin egg into which R-ODN-F (having a natural phosphodiester linkage) has been injected.
Figure 10B:
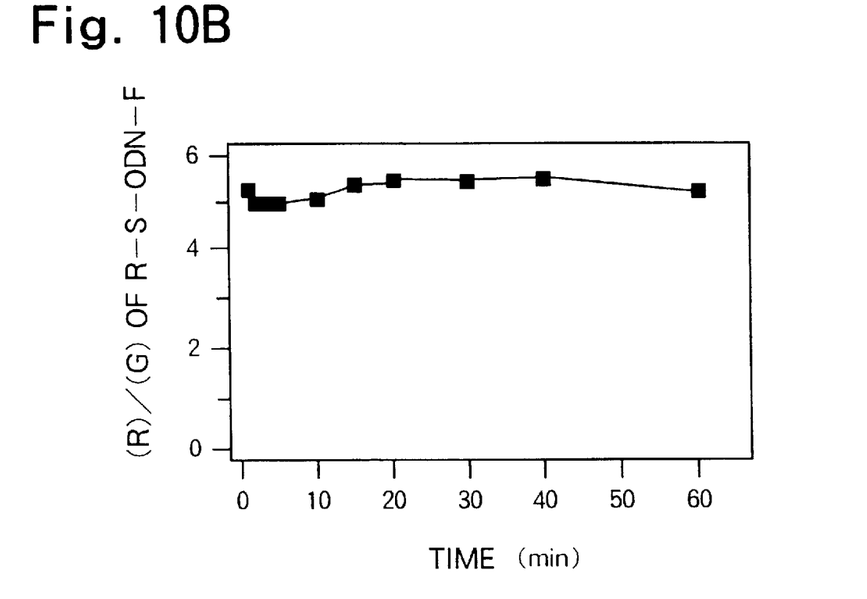
FIG. 10B is a chart showing the change in the ratio in a sea urchin egg into which R-S-ODN-F (having a nuclease-resistant phosphorothioate linkage) has been injected.

(Example 2)
Synthesis of 5'-Fluorescein-TGAAATTGTT-3'-Rhodamine X (F-ODN-R) (FIG. 8)

Figure 2:
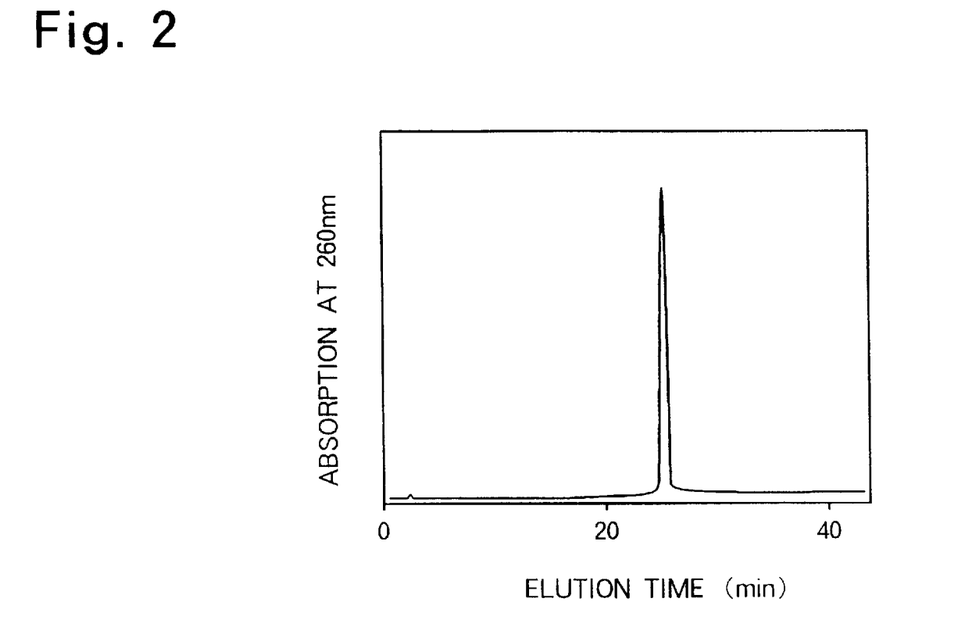
FIG. 2 is a chart showing a high-pressure liquid chromatogram of 5'-fluorescein-TGAAATTGTT-3'-rhodamine X (F-ODN-R) after purification and separation.

It was synthesized by a chemical synthesis method and a single peak was confirmed therein according to HPLC (FIG. 2).

(Absorption Spectrum and Fluorescence Spectrum)

F-ODN-R was diluted to an appropriate concentration by solvent A (50-mM Tris-HCl buffer solution at pH 8.0, 0.1 M of NaCl, 1 mM of $CaCl_2$, and 1 MM of $MgCl_2$).

Its absorption spectrum and fluorescence spectrum were obtained by a spectrophotometer (Hitachi model 557) and a fluorescence spectrophotometer (Hitachi model 850), respectively.

Figure 3:
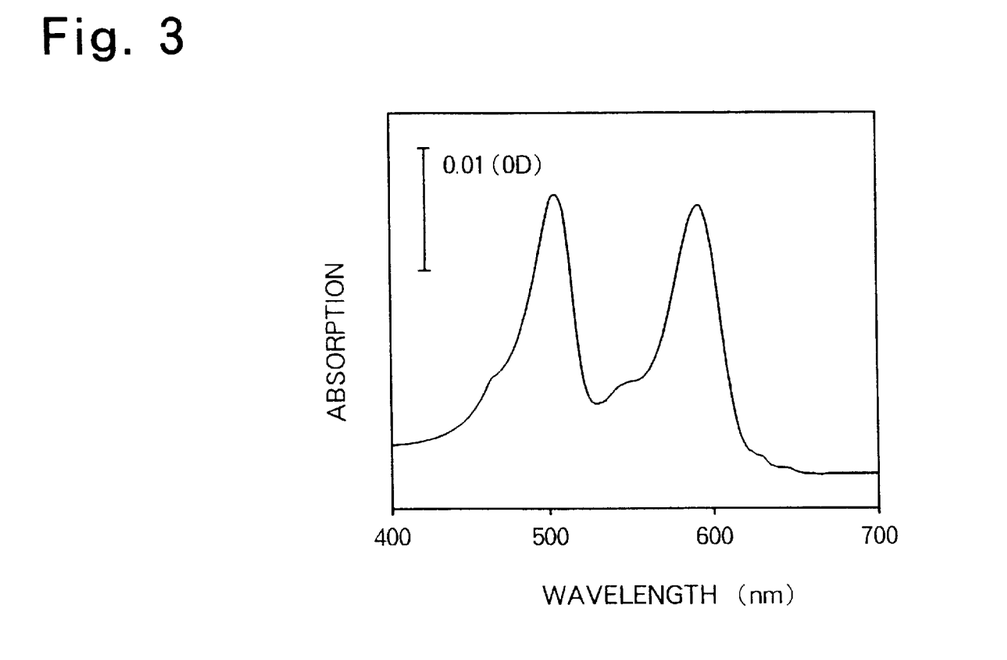
FIG. 3 is a chart showing an absorption spectrum of 5'-fluorescein-TGAAATTGTT-3'-rhodamine X (F-ODN-R)

As shown in FIG. 3, the absorption spectrum of FODN-R coincides with an absorption spectrum obtained when respective absorption spectra of fluorescein and rhodamine X are superposed on each other.

Figure 4:
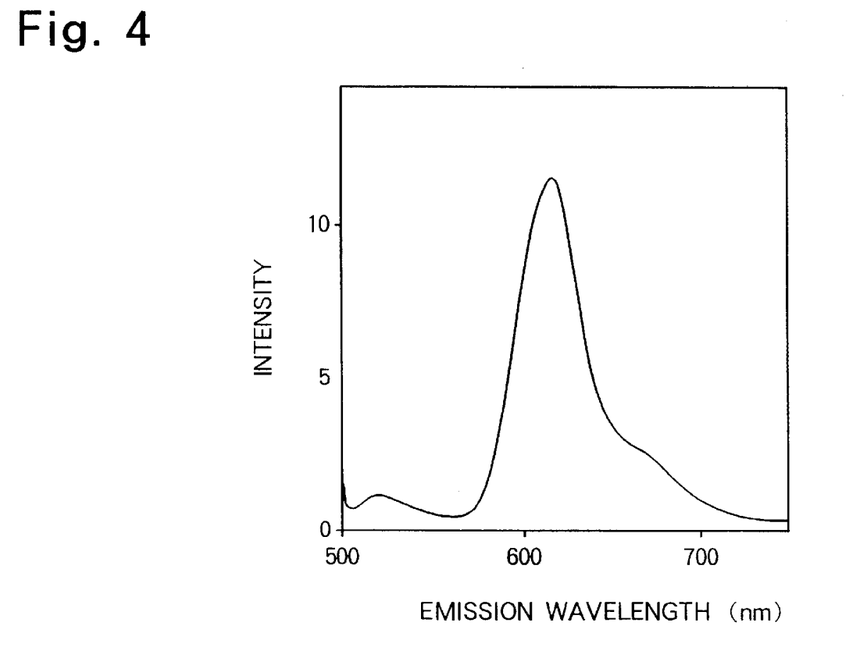
FIG. 4 is a chart showing an emission spectrum of 5'-fluorescein-TGAAATTGTT-3'-rhodamine X (F-ODN-R) exited at 494 nm.

FIG. 4 shows a fluorescence spectrum of F-ODN-R.

When excited at 494 nm, it exhibits fluorescence peaks at 523 nm and 610 nm which correspond to respective fluorescence spectra of fluorescein and rhodamine X superposed on each other.

Figure 5:
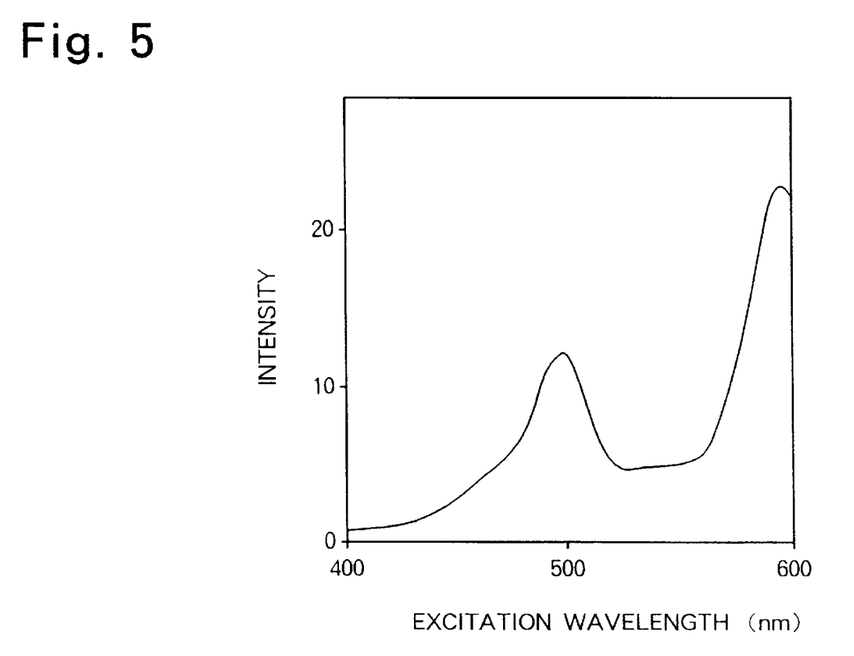
FIG. 5 is a chart showing an excitation spectrum of 5'-fluorescein-TGAAATTGTT-3'-rhodamine X (F-ODN-R) monitored at 606 nm.
Figure 6:
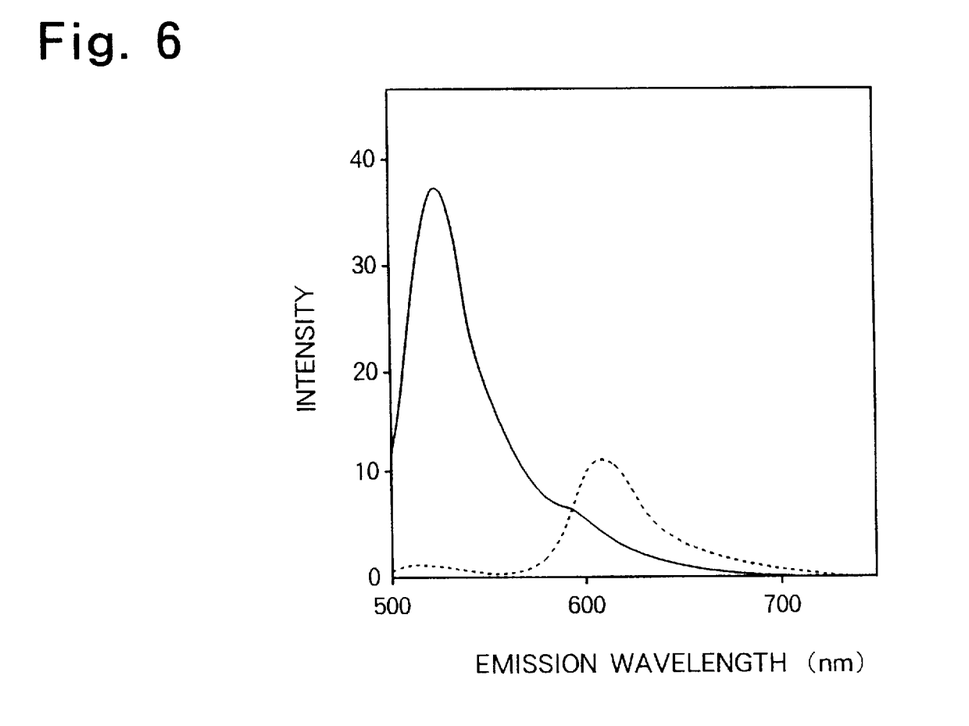
FIG. 6 is a chart showing (as continuous curve) an emission spectrum of 5'-fluorescein-TGAAATTGTT-3'rhodamine X (F-ODN-R) before (solid line) and after (dotted line) enzymatic digestion with BAL31.

Similarly, when monitored at 606 nm, it provides excitation peaks at 500 nm and 594 nm(FIG. 5).

When their respective fluorescence intensity values are compared with each other, it is found that, upon excitation at 494 nm, the intensity of the fluorescence spectrum derived from rhodamine X at 610 nm is several times as much as that derived from fluorescein.

This result suggests that the excitation energy of the fluorescein fluorogen has transferred to the rhodamine fluorogen, thereby changing their fluorescence intensity values.

(Digestion of Oligonucleotide by Enzyme)

Thus obtained oligonucleotide (F-ODN-R), as a substrate, was digested by BAL31 nuclease (manufactured by Takara Shuzo) having a function as endonuclease for single-chain DNAs (Sambrook, J., Fritsch, E. F., and Maniatis, T. Molecular Cloning: A Laboratory Manual. Cold Spring Harbor Laboratory Press, Cold Spring, 1989).

For example, measurement in vitro was performed after the F-ODN-R (17 nM) in 2 ml of solvent A had been incubated with 5 units of BAL31 at 30° C. for 60 minutes.

Alternatively, measurement in vivo was performed after the F-ODN-R (50 $\mu$M) in 4 pl of solvent A had been incubated with 0.1 unit of BAL31 at 30° C. for 30 minutes.

The digestion by this enzyme was stopped when 2 $\mu$l of 0.1-M EGTA was added to 4 $\mu$l of the reaction solution.

(Sea Urchin Eggs and Microinjection)

Eggs of a sea urchin (*Hemicentrotus pulcherrimus*) were collected as 0.55-M KCl was injected into its body cavity and then washed twice with seawater. The eggs were disposed on a poly-L-lysine-coated glass cover slip (with frames made of Lucite forming a chamber having a capacity of about 3 ml).

The oligonucleotide was suspended to a concentration of 100 $\mu$M in 100-mM HEPES-KOH at pH 7.2 and thus formed oligonucleotide solution (about 1 to 2% with respect to the egg volume) was microinjected into the eggs (Hirano, K. Develop. Growth and Differ. 24, 1982, 273–281).

(Visualization of FRET under Microscope)

In order to observe the FRET phenomenons resulting from thus obtained sea urchin eggs, 2 filters provided for a fluorescence microscope (Diaphoto-TMD, manufactured by Nikon) were respectively used for observing the fluorescence ingredients derived form the injected oligonucleotide.

Green images were observed through a band-pass filter of 520 to 560 nm, whereas red images were observed through a sharp-cut filter of 580 nm and over.

A heat-absorbing filter was used to eliminate infrared rays from both of these types of images.

The excited light obtained through a band-pass filter of 470 to 490 nm was eliminated from the observed fluorescence signal (with a cut-off wavelength of 510 nm by a dichroic mirror).

Thus obtained green and red images were captured by a highly sensitive ICCD camera (c2400-80, manufactured by Hamamatsu Photonics) and the fluorescence intensity was processed and analyzed with an image processor (ARGUS-50, manufactured by Hamamatsu Photonics).

The sea urchin egg to which the oligonucleotide had been microinjected exhibited bright red fluorescence in addition to the green fluorescence derived from fluorescein.

By contrast, no red fluorescence but only green fluorescence was observed in the sea urchin egg into which the BAL31-digested product had been injected.

The fluorescence intensity varied among parts of the egg. Namely, the intensity was stronger at the center of the egg, while both green and red were weaker at the periphery. This problem resulted from differences in optical path length and could be corrected when the cell volume was amended.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application No. 050926/1995 (7-050926) filed on Mar. 10, 1995 is hereby incorporated by reference.

What is claimed is:

1. A method of measuring decomposition of a single-stranded oligonucleotide by endonuclease activity, wherein the oligonucleotide comprises an energy donor group and an energy acceptor group positioned sufficiently close so as to have overlapping energy spectrums, and a restriction site recognizable by an endonuclease, which restriction site is positioned between the energy donor group and the energy acceptor group, which method comprises the steps of
(i) detecting a resonance energy transfer between the energy donor group and the energy acceptor group; and
(ii) detecting a loss in the resonance energy transfer, which loss indicates decomposition of the oligonucleotide by endonuclease activity at the restriction site.

2. The method of claim 1, wherein the energy donor group and energy acceptor group are each positioned at one of a 5'- or a 3'- terminal of the oligonucleotide.

3. The method of claim 1, wherein the energy donor group and energy acceptor group are fluorogens positioned sufficiently close so as to have overlapping energy spectrums, and the method comprises the steps of
(i) detecting a fluorescence resonance energy transfer between the energy donor group and the energy acceptor group; and
(ii) detecting a loss in the fluorescence resonance energy transfer, which loss indicates a decomposition of the oligonucleotide by endonuclease activity.

4. The method of claim 3, wherein the energy donor group and energy acceptor group are each positioned at one of a 5'- or a 3'- terminal of the oligonucleotide.

5. The method according to claim 3, wherein said energy donor group contains a fluorescein fluorochrome, while said energy acceptor group contains a rhodamine fluorochrome.

6. The method according to claim 3, wherein the oligonucleotide chain between said set of energy donor group and energy acceptor group comprises not less than 3 but not more than 20 nucleic acid bases.

7. The method according to claim 3, wherein the oligonucleotide chain between said set of energy donor group and energy acceptor group has a length of 10 nucleic acid bases.

8. The method according to claim 4, wherein said energy donor group contains a fluorescein fluorochrome, while said energy acceptor group contains a rhodamine fluorochrome.

9. The method according to claim 4, wherein the oligonucleotide chain between said set of energy donor group and energy acceptor group comprises not less than 3 but not more than 20 nucleic acid bases.

10. The method according to claim 4, wherein the oligonucleotide chain between said set of energy donor group and energy acceptor group has a length of 10 nucleic acid bases.

* * * * *